United States Patent [19]

Boige

[11] 4,048,303

[45] Sept. 13, 1977

[54] METHOD OF PREPARING ENZYME CHOLIC ACIDS COMPLEX

[75] Inventor: Jean Boige, Aulnay sous Bois, France

[73] Assignee: L'Opochimie, Fontvieille, Monaco

[21] Appl. No.: 630,763

[22] Filed: Nov. 11, 1975

[30] Foreign Application Priority Data

Nov. 29, 1974 United Kingdom ............... 51853/74

[51] Int. Cl.$^2$ ..................... A61K 37/48; A61K 35/38
[52] U.S. Cl. ........................................ 424/94; 424/104
[58] Field of Search .................................. 424/94, 104

[56] References Cited

FOREIGN PATENT DOCUMENTS

561,333   5/1944   United Kingdom

OTHER PUBLICATIONS

Advances in Lipid Research, vol. 10 (1972), pp. 102–141, Academic Press, N.Y.

*Primary Examiner*—Donald B. Moyer
*Attorney, Agent, or Firm*—Young & Thompson

[57] ABSTRACT

A stable enzyme hormone complex is prepared by extraction from the small intestines of animals. In accordance with the invention the extraction is carried out using cholic acids and polyethylene glycol mono-para (1,1,3,3 tetramethyl butyl) phenyl ether.

3 Claims, No Drawings

METHOD OF PREPARING ENZYME CHOLIC ACIDS COMPLEX

The invention relates to a method of preparing a stable enzyme-hormone complex by extraction from the small intestine of animals such as pigs and bullocks.

As is known, the two parts of the small intestine, i.e. the duodenum and jejunum, produce pro-enzymes, enzymes and hormones which play an important part in digestive metabolism and the assimilation of food.

The enzymes in the duodenum contain e.g. disaccharidases which release glucose from disaccharides, dipeptidases which break up dipeptides and include leucylprolinase whoch releases leucine, and, more particularly, enterokinase, the enzyme capable of activating the trypsinogen and chymotrypsinogen in the pancreas. The jejunum does not contain enterokinase, but larger quantities of some saccharases.

it is therefore desirable to develop a method of extracting these enzymes, pro-enzymes and hormones from the whole small intestine without denaturing them, so that they retain their entire activity and can be processed in the form of drugs.

It is known that if the intestine is taken and crushed, a considerable part of the desired activity disappears, so that if the liquid obtained by crushing the intestine is simply collected, it is found that a considerable proportion of enzymes or hormones are not present, since they are inside the muscular tissue cells or attached to the brush-like edge of the intestine. More particularly, it has been shown that interokenase occurs largely in the internal wall of the duodenum. It is found that the endocellular enzymes and the enzymes intimately fixed to the external tissue of the intestine are not extracted to any appreciable extent by simple aqueous extraction of the intestine.

When organic solvents are used for extraction, the desired products are frequently denatured or made inactive. Some enzymes or hormones are almost completely lost during precipitation, through denaturation or inactivation.

An object of the invention is to obviate these disadvantages by providing a process of obtaining an enzyme-hormone complex containing nearly all the enzymes and hormones in the small intestine with their initial activity, with a view inter alia to using the complex as a drug for treating intestinal diseases due to enzyme or hormone deficiency.

The invention relates to a method of preparing a stable enzyme-hormone complex from the small intestine, characterised in that an aqueous solution of cholic acids and polyethylene glycol mono-para (1,1,3,3 tetramethyl butyl) phenyl ether is reacted with fresh or refrigerated small intestine, after which the small intestine is separated from the liquid, in which the enzymes and hormones have dissolved.

The term "cholic acids" is used to denote the series of bile acids comprising cholic acid (formula $C_{24}H_{40}O_5$, or its derivative desoxycholic acid, and compounds resulting from the combination of cholic acid with amino acids, e.g. glycocholic acid $C_{26}H_{43}O_6N$ or taurocholic acid $C_{26}H_{45}O_7SN$.

Polyethylene glycol mono-para (1,1,3,3 tetramethyl butyl) phenyl ether is more generally known under the name TRITON X 100 (mark registered by Messrs. MERCK), a wetting agent.

Unexpected results are obtained by the combined use of the two products in solution in water for extracting enzymes and hormones. It has been found that the two products have complementary physical properties and that their extractive effect is considerably increased owing to the ease with which the ether can extract the enzymes fixed in the brush-like edge of the intestine or in the cells of the intestinal wall.

The cholic acids and ether also have the advantage of not chemically reacting with the intestinal enzymes and hormones.

Thus, in the method according to the invention, the enzymes and hormones can be dissolved and therefore almost completely extracted. The solution can be used without treatment, or can be purified by dialysis followed by lyophilization so as to obtain a dry powdered extract.

The proportion of aqueous solution with respect to the weight of treated intestine can vary within wide limits, e.g. between 1 and 2.5 liters of solution per kg of intestine. The preferred ratio, however, is 1 liter of solution per kg of intestine, thus avoiding the need to eliminate an excessive amount of liquid.

The amounts of cholic acid and polyethylene glycol mono-para (1,1,3,3 tetramethyl butyl)phenyl ether dissolved in water can vary between 100 and 600 g for the first compound and 50 and 400 ml for the second compound, 100 liters of water.

Preferably, before the small intestine is mixed with the aqueous solution containing the aforementioned compounds, it is cut into pieces to facilitate the extraction of the enzymes and hormones but is not further crushed, since this would destroy a considerable part of the enzyme and hormone activity.

Preferably, also, after the intestine has been mixed with the extraction solution, the pH of the mixture is adjusted to between 6 and 7, since it has been found that below pH 6 (inter alia below pH 5) enterokinase is inactivated, whereas above pH 7 there is a risk of autodigestion of proteins and, more particularly, degradation of the enzymes.

Preferably the extraction is made at room temperature under agitation for 2 hours, after which the mixture is left to stand for 12 hours at a temperature between 0° and 5° C. Advantageously, the mixture after extraction is filtered through a large cloth to separate the larger pieces, after which the filtrate is centrifuged.

The following non-limitative example is described for the sole purpose of illustrating the method according to the invention.

In this example, 100 kg of pig's small intestine was used, after being broken to −10° C and stored at this temperature until the time of extraction. After the temperature of the intestine had been brought to approximately 0° C, it was cut in a mincer and dissolved in 100 l of water containing 100 cm³ TRITON X 100 and 200 g cholic acids. The pH was adjusted to between 6 and 7 and the mixture was agitated for 2 hours and then left to stand overnight at 0° C. It was filtered and the filtrate was centrifuged. The residue was exhausted by washing with 20 l water. The combined liquids were again filtered, then centrifuged by passing through "reverse dialysis" columns comprising porous discs through which molecules having a molecular weight lower than approximately 1000 can pass. The initial volume of liquid, which was between 200 and 250 l, was reduced by concentration to approximately 30 l. About 40% of the initial dry material was eliminated together with the water, by dialysis through the column.

The concentrated liquid was analyzed and found to contain all the active enzymes and hormones. After the liquid had travelled through a dialyzer, it was lyophilized, yielding 4 kg of lyophilized dry powder which easily dissolved.

The enzyme-hormone complex was analyzed by the following methods:

ENZYMES

The units of enterokinase were titrated by the Kunitz method (Methods in Enzymology, Colowick-Kaplan, No. 2, page 32) which consists in activating trypsinogen to trypsin using enterokinase; one unit of enterokinase is defined as the quantity which activates 0.065 mg trypsinogen at pH 5.8 at 5° C for an hour.

The alkaline phosphatase was determined by the method of O. A. Bessey, H. Lowry and M. J. Brock (Division of nutrition and physiology, Public Health Research Institute of New York) published on Mar. 28, 1946.

The methods indicated in "Methods in Enzymology" cited hereinbefore were used to determine maltase (following Dahlquist, volume 8, page 584), lactase, sucrase, trehalase and ornithine carbamyl transferase (volume 17, BP 885).

The content of gamma-glutamyl transferase was determined by the Nerville method and the content of aminopeptidase by the method of G. Proncari and Zuber (Inter 5 Protein Alsearch 1,45).

The measurements were as follows, expressed in units/mg and made on the product after using the method in the preceding example:

| Enterokinase | 8 | u/mg |
|---|---|---|
| Maltase | 110 | u/mg |
| Trehalase | 2.4 | u/g |
| Alkaline phosphatase | 25 | u/g |
| Aminopeptidase | 12 | u/g |
| Glutamyl transferase | 0.5 | u/g |

Appreciable quantities of ornithine carbamyl transferase, saccharase and lactase.

Of course, these proportions vary from one test to another, inter alia depending on the quantity of cholic acids and Triton X 100 used.

The tests, however, showed that in all cases the following results were obtained by varying the quantity of cholic acids between 100 and 600 g and the quantity of Triton X 100 between 50 and 400 ml per 100 kg intestine and 100 liters water:

| Enterokinase | 8 - 12 u/mg |
|---|---|
| Maltase | >40 u/mg |
| Alkaline phosphates | >10 u/mg |
| Aminopeptidase | >2 u/mg |

HORMONES

The main hormones detected in the complex obtained were enterogastrone, secretin, cholecystokinin, caerulein and pacreozymin.

Undoubtedly the complex has hormone activity since, when it is administered in therapy, the intestinal contractions are found to be inhibited.

Comparative tests were made so as to show the technical results obtained by the method according to the invention.

The test conditions were as follows:

5 batches of small intestine, each weighing 100 kilograms, were collected and immediately frozen at −20° C. After being stored for a time, they were slowly unfrozen until the entire mass was at a temperature between 0° and −5° C.

The batches were cut with an electric knife. 5 extraction media were prepared, each containing 100 liters of water. The first extraction bath was pure water, whereas the quantities of products stated hereinafter were dissolved in the other four baths.

The results are expressed in units per milligram whereas the quantity of dry extract is given as a percentage of the quantity of raw material used.

|  | Water only | 600 g cholic acid only per 100 kg intestine | 400 ml of Triton only per 100 kg intestine | Tests according to the invention | |
|---|---|---|---|---|---|
|  |  |  |  | 200 g cholic acid and 100 ml Triton per 100 kg intestine | 600 g cholic acid and 300 ml Triton per 100 kg intestine |
| Dry extract obtained | 2% | 3% | 4% | 6% | 6% |
| Enterokinase | 1 u | 3 u | 3 u | 5 u | 5 u |
| Alkaline phosphatase | 10 u | 10 u | 15 u | 20 u | 20 u |
| Aminopeptidase | 5 u | 5 u | 10 u | 12 u | 12 u |

As can be seen, the extraction yield is considerably higher, with regard both to the amount of extracted material and the concentration in enzyme units, when an extraction solution obtained by the method according to the invention is used. It can also be seen that no improvement is obtained by using more than 200 g cholic acid or more than 100 ml of Triton X 100 per 100 kg intestine.

The liquid obtained after extraction was again filtered on a cloth and then concentrated by passing it through dialysis columns provided with discs through which molecules having a molecular weight less than approximately 1000 could pass.

A large proportion of the salts, Triton X 100 and degradation products were separated in this manner, followed by dialysis and lyophilization.

No loss was observed with respect to the quantities determined after the first extraction, and there was no decrease in activity.

The invention also relates to a drug wherein the active substance is the enzyme-hormone extract obtained by the method according to the invention.

Toxicity tests on the drug, made on rats, showed that the extract according to the invention did not have any acute or chronic toxicity.

The extract obtained according to the example was administered to rats having an average weight of 250 kg, by luminal perfusion in a dose of 0.5 mg in 1½ hours.

Next, the enzyme secreted by the rats were measured. It was found that the quantity of trypsin, chymotrypsin and lipase secreted was 3 or 4 times greater than the quantity initially present in the rats.

In another test, the extract was intraarterially administered to rats in the form of a solution containing 2.5 mg of extract in 10 ml, at the rate of 0.2 ml per 10 min., i.e. a total of 0.5 mg of extract per rat.

The result was a rapid increase in the proportion of saccharase and alkaline phosphatase and a vasodilation comparable with that obtained by administering hormones such as entergastrone, secretin, cholecystokinin, caerulin and pacreozymin.

The extract according to the invention was also orally administered. Half an hour later, the motor activation of the intestine slowed down considerably, thus improving the use of the digestive enzymes.

A first series of medical tests was made on 10 patients suffering from gastroenteric disorders involving creatorrhoea which is the presence of muscle fibers in the feces.

These patients were orally treated with capsules containing the extract according to the invention in doses between 50 and 200 mg per meal for 10 days.

The test series was made at the same time as a control drug (capsules containing a placebo) were administered.

After the tests, the amount of nitrogen and fats was measured in the excreta of each patient.

The results are shown in the Table I.

The results in the Table show that the assimilation of fats and proteins was considerably improved in most cases treated with the drug according to the invention. This remarkable result may be due to the fact that the extract according to the invention increases the proportion of lipase, the enzyme which assimilates lipids.

In a second test series, 9 patients were treated with capsules in doses of 150 enzyme extract per day, i.e. 50 mg per meal.

The steatorrhoea was measured before and after treatment.

The test results are shown in the Table II. As can be seen, there was a considerable decrease in steatorrhoea in all cases.

The clinical tests results show that the enzyme extract according to the invention provides a substitute treatment in all cases where the intestine has been medically or surgically removed and in all cases where the intestine has been injured.

The dose of the drug for treating these conditions varies between 50 and 200 mg of enzyme extract per meal, i.e. 150 and 600 mg per day, depending on age, weight and the nature of the condition.

Preferably, the drug is administered in the form of capsules or tablets each containing 50 or 100 mg of enzyme extract and releasing the extract only when the drug is in the patient's stomach.

The following are two preferred examples of pharmaceutical forms of the drug according to the invention:

1) Capsule:
   Enzyme-hormone extract: 100 mg
   Starch: 25 mg
   Casing: keratin 2) Tablet:
   Enzyme-hormone extract: 50 mg
   Powdered keratin: 25 mg
   Excipient for compression: q.s. for 100 mg

TABLE I

| Patient | Age | Diagnosis | Nitrogen in g/24 hours | | Fats in g/24 hours | |
|---|---|---|---|---|---|---|
| | | | CE | P | CE | P |
| 1 | 17 years | DE | 3.2 | 5.8 | 13.0 | 15.2 |
| 2 | 65 years | D.P. | 2.1 | 3.8 | 45.5 | 45.0 |
| 3 | 68 years | D.a.I. | 1.87 | 5.0 | 40.3 | 83.0 |
| 4 | 57 years | D.a.I. | 0.22 | 0.9 | 0.6 | 2.3 |
| 5 | 71 years | D.P. | 1.9 (2.0) | 3.2 (3.0) | 20.8 | 15.2 |
| 6 | 63 years | D.P. | 3.8 | 4.0 | 23.4 | 33.5 |
| 7 | 49 years | D.a.I. | 3.1 | 4.2 | 11.0 | 21.0 |
| 8 | 9 years | res. n. Il. | 1.5 | 3.5 | 9.0 | 15.0 |
| 9 | 16 years | Cr. | 2.3 | 4.9 | 35.0 | 54.0 |
| 10 | 68 years | D.P. | 5.2 | 5.1 | 20.0 | 19.6 |

The following abbreviations are used in the Table:
CE = enzyme complex according to the invention
D.a.I. = diarrhoea after irradiation
P = placebo
res. n. Il. = neonatal resection of ilium
DE = deficit in enterokinase
Cr. = Crohn's disease
D.P. = duodenopancreatectomy

TABLE II

| Patient | Age (Years) | Diagnosis | Steatorrhoea before treatment, g/24 hours | Steatorrhoea after treatment g/24 hours | Variations |
|---|---|---|---|---|---|
| 1 | 52 | Cirrhosis Digestive haemorrhage | 24.91 | 9.83 | −60% |
| 2 | 47 | Chronic pancreatitis + ectomy of pancreatic duct and jejunum +cholecystectomy | 7.55 | 7.35 | − 3% |
| 3 | 50 | Chronic pancreatitis | 21.75 | 9.79 | −55% |
| 4 | 56 | Ethyl cirrhosis | 6.76 | 5.57 | −17% |
| 5 | 66 | Macronodular cirrhosis | 8.73 | 6.55 | −25% |

TABLE II-continued

| Patient | Age (Years) | Diagnosis | Steatorrhoea before treatment, g/24 hours | Steatorrhoea after treatment g/24 hours | Variations |
|---|---|---|---|---|---|
| 6 | 41 | Gastric ulcer, ethyl cirrhosis | 7.96 | 1.31 | −83% |
| 7 | 35 | Chronic pancreatitis | 7.80 | 4.01 | −48% |
| 8 | 41 | Crohn's disease | 8.08 | 7.06 | −12% |
| 9 | 61 | Acute pancreatitis haemorrhage, diarrhoea owing to antibiotic treatment | 9.39 | 9.01 | − 4% |

We claim:

1. A method of preparing an enzyme-hormone complex containing between approximately 8 and 12 units/mg of enterokinase, more than 40 units/mg of maltase, more than 10 units/g of alkaline phosphatase, more than 2 units/mg of aminopeptidase and trehalase, glutamyl transferase, ornithine carbamyl transferase, saccharase, lactase, enterogastrone, secretin, cholecystokinin, caerulin and pancreozymin, from the small intestine of pigs or bullocks, comprising the steps of:
   a. mixing pieces of fresh or refrigerated small intestine with an aqueous solution containing between 100 and 600 g of cholic acids constituted by a mixture of cholic acid, desoxycholic acid, glycocholic acid and taurocholic acid and between 50 and 400 ml of polyethylene glycol mono-para (1,1,3,3 tetramethyl butyl)phenyl ether per 100 liters of water, the proportion of said aqueous solution being between about 100 and about 250 liters per 100 kg of small intestine;
   b. maintaining the resulting mixture for about 2 to about 12 hours at a temperature between 0 to 5° C and at a pH of about 6 to 7; and
   c. separating from the mixture the treated pieces of small intestine by filtration in order to obtain a solution containing said enzymes and hormones.

2. A method according to claim 1, and purifying the obtained solution by dialysis so as to remove the molecules having a molecular weight higher than about 1000, and lyophilizing the purified solution so as to obtain a dry powder.

3. A method according to claim 1, wherein 100 kg of pieces of small intestine taken from a pig are mixed with 100 liters of water containing 100 g of cholic acids and 100 ml of mono-para(1,1,3,3 tetramethyl butyl)phenyl ether.

* * * * *